United States Patent [19]

Kelly, deceased et al.

[11] 4,147,776
[45] Apr. 3, 1979

[54] STABILIZED CHOLINE SALICYLATE COMPOUNDS

[75] Inventors: William Kelly, deceased, late of Liverpool, England, by Monica Kelly, personal representative; by John Kelly, personal representative, Great Saukey, England; Alfred Halpein, Lake Success, N.Y.

[73] Assignee: Mundipharma, AG, Rheinfelden, Switzerland

[21] Appl. No.: 880,840

[22] Filed: Feb. 23, 1978

Related U.S. Application Data

[62] Division of Ser. No. 753,396, Dec. 22, 1976, Pat. No. 4,098,813, which is a division of Ser. No. 625,783, Oct. 24, 1975, Pat. No. 4,001,311, which is a division of Ser. No. 501,004, Sep. 3, 1974, Pat. No. 3,947,491, which is a division of Ser. No. 237,927, Mar. 24, 1972, Pat. No. 3,855,282.

[30] Foreign Application Priority Data

Jul. 24, 1971 [GB] United Kingdom ............... 34941/71

[51] Int. Cl.$^2$ ..................... A61K 31/00; A61K 31/60
[52] U.S. Cl. ................................... 424/175; 424/230
[58] Field of Search ............................... 424/175, 230

[56] References Cited

FOREIGN PATENT DOCUMENTS 1956626 5/1971 Fed. Rep. of Germany.
1567793 5/1969 France.

*Primary Examiner*—Stanley J. Friedman
*Attorney, Agent, or Firm*—Wolder, Gross & Yavner

[57] ABSTRACT

Choline salicylate sulfite and choline salicylate alkali metal sulfite-containing compounds of the formula;

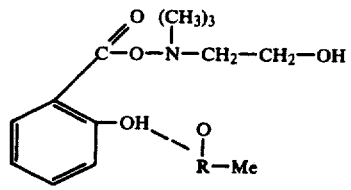

wherein Me represents the sodium, potassium, or lithium ion and R represents the sulfite bisulfite metabisulfite, dithionate, hydrosulfite, and hyposulfite groups are described. Said compounds are stable and inhibit the formation of color on pharmaceutical preparations containing the same. The method for the preparation of cholin-salicylate sulfite and choline salicylate alkali metal sulfite-containing compounds, and pharmaceutical dosage forms containing the same are disclosed together with a method for their use to inhibit color formation.

16 Claims, No Drawings

STABILIZED CHOLINE SALICYLATE COMPOUNDS

This application is a division of Ser. No. 753,396, filed Dec. 22, 1976, now U.S. Pat. No. 4,098,813; which is a division of Ser. No. 237,927, filed Mar. 24, 1972, now U.S. Pat. No. 3,855,282; which is a division of Ser. No. 501,004, filed Sept. 3, 1974 now abandoned; which is a division of Ser. No. 237,927, filed Mar. 24, 1972, now abandoned.

This invention relates to stabilized compounds of chlorine salicylate, the method for producing the same and pharmaceutical compositions containing the aforesaid stabilized compounds. In particular it relates to a molecular coordination compound formed between choline salicylate and an alkali metal sulfite-containing compound and/or sulfur dioxide, the method for the preparation of aforesaid compounds and pharmacoustical compositions containing the same as well as the methods for the use of said pharmaceutical compositions.

Choline salicylate is described in U.S. Pat. No. 3,069,321, (Dec. 18, 1962). Choline salicylate has unique advantages over other salicylate compounds and it has been introduced into therapy as an active ingredient of a large number of pharmaceutical dosage forms including solutions, syrups, ointments, gels, lonzenges, tablets, capsules and suppositories.

An inherent disadvantge to the use of choline salicylate in both pharmaceutical manufacture and therapy is the appearance of a color in formulations containing choline salicylate, whether prepared in aqueous or non-aqueous solvents; liquid or solid dosage forms. This color formation necessitates manufacture of multiple batches to avoid storing the compound for extended periods, thereby increasing costs through multiple handling operations. The appearance of a color in a finished pharmaceutical dosage-form causes confusion and concern to the patient, who is unaware of the nature of this change, thereby possibly interrupting therapy.

Although the exact cause of color formation in choline salicylate formulations is not known and various theories for its origin have been proposed, it is generally accepted than an electron shift in molecular configuration takes place to produce a chromophore. It is an object of the present invention to prevent, as well as to substantially reduce, the formation of color in choline salicylate preparations, whether in liquid or solid dosage form, or in bulk preparations intended to be used in further manufacture.

It was found that the suppression or avoidance of the aforesaid color formation in compositions containing choline salicylate may be achieved through the formation of a molecular coordinate compound between choline salicylate and an alkali metal sulfite-containing compound as for example, sodium bisulfite ($NaHSO_3$), sodium metabisulfite ($Na_2S_2O_5$), sodium hydrosulfite ($Na_2S_2O_4$), sodium dithionate ($Na_2S_2O_6 2H_2O$), sodium hyposulfite ($Na_2S_2O_2$) and sodium sulfite ($Na_2SO_3$) or the corresponding lithium and potassium salts. Sulphur dioxide also forms a molecular compound with choline salicylate and therefore the point of coordination may be said to be through the sulfite group. The new molecular coordination compounds may be considered to inhibit the electron shift necessary to form a chromophore and thereby inhibit color formation. According to one aspect of the invention therefore, there is provided as a new composition of matter, the composed formed between choline salicylate and an alkali metal sulfite-containing compound and sulfur dioxide as well as compositions comprising the same, said composition being substantially free from color formation.

The formation of the new molecular coordination compound between an alkali metal sulfite-containing compound and choline salicylate is established through the change in specific electrical conductance of a solution containing said compound. When two or more substances are introduced into the same solvent, the specific electrical conductivity of the mixture will be generally expressed as the arithmetic sum of the number of ions present in solution. However, if molecular complexing occurs among the molecules in solution, then this is reflected in the nature of the change observed in specific electrical conductivity for the mixture.

If the specific electrical conduction of a mixture of substances in solution is greater than the additive sum of the separate conductivity values of the components, then this establishes that a new molecular change has taken place to increase the electrical conductivity of the new molecule in solution. The presence of the newly formed compound is demonstrated through the increase in specific electrical conductivity since it possesses a property that is different from the mixture of the separate component substances.

If the specific electrical conductivity of the mixture is less than the arithmetic sum of the individual conductivity values determined for the component in solution, then a new molecular compound is formed that has a reduced electrical conductivity or a decreased ionizing potential in solution. This may occur through an internal electron sharing resulting in a depressed level of ionization for the new compound. Such complexing has been observed after the formation of chelate compounds.

When no new chemical bond results so that there is no modification in the electrical conductivity of the mixture of substances in solution, then the specific electrical conductivity for the mixture remains substantially the additive sum of the values for the separate moieties.

The method used in determining the specific electrical conductance of a solution is to measure the degree of resistance encountered to the flow of a standard electrical current through an accurately measured volume of solution. The resistance to the flow of electrical current (ohms) is determined for a volume of the conductor solution 1 cm long at each edge. The specific conductance of the solution is thereby computed as the reciprocal of the specific resistance and is expressed in units termed mhos, the reciprocal of ohms.

When the specific electrical conductivity of choline salicylate in aqueous solution was determined, it was found that an 0.5 molar solution of choline salicylate has an electrical resistance of 2.3 ohms and a specific conductance of 0.035 mhos/cm. The electrical resistance determined for an 0.5 molar solution of sodium busulfite was 0.8 ohms and the specific electrical conductance was computed to be 0.10 mhos/cm. However, when an 0.5 molar solution of choline salicylate was reacted with an 0.5 molar solution of sodium bisulfite, the specific electrical conductivity determined it was found to be 0.007 mhos/cm. This value is markedly less than the expected arithmetic sum of the separate electrical conductivity values for the mixture of components. The calculated arithmetic sum of the specific electrical conductance of the components in the aforesaid mixture is 0.009 mhos/cm. This demonstrates that a new molecule formed between choline salicylate and sodium bisulfite which possessed a decreased ionizing potential different from that expected for a mixture of choline salicylate and sodium bisulfite.

In a similar manner it was found that an increase in the electrical resistance occured with a consequent decrease in specific electrical conductivity when other alkali metal sulfite compounds were caused to react with choline salicylate. Thus, when such compounds as sodium dithiomate ($Na_2S_2O_6$), sodium metabisulfite ($Na_2S_2O_5$), sodium hydrosulfite ($Na_2S_3O_4$), sodium sulfite ($Na_2SO_3$), and sodium hyposulfite ($Na_2S_2O_2$), or the respective corresponding lithium and potassium sulfite salts are reacted with choline salicylate, a new composition of matter formed having different properties than the mixture of its components. It was further found that new compound formation apparently takes place through the sulfite radical. Gaseous sulfur dioxide also reacted with choline salicylate to produce a new compound, choline salicylate sulfite. The aforesaid new compounds do not exhibit color formation on storage and when added to phenolic color forming compounds block or suppress the formation of a color.

The new compounds are preferably formed concurrently with the synthesis of choline salicylate, although the new compounds will form when the appropriate sulfite-containing reagent is reacted with formed choline salicylate. The new compound formed between choline salicylate and the respective alkali metal sulfite-containing salts or sulfur dioxide may be in the form of the solid choline salicylate-sulfite compound or present in solution. When the new compositions are formed at the time of the synthesis of chloline salicylate, then the appropriate sulfite-containing compound, described above, is dissolved in the aqueous medium or polar solvent used as the medium for the reaction. When the new compound is desired to be formed, after the synthesis of choline salicylate, then the appropriate sulfite-containing compound described above is added to the formed choline salicylate either in solution or in the dry form. However, minimal quantities of water are preferred when forming the new choline salicylate alkali metal sulfite-containing compounds. The commercial grade of the respective sulfite-containing compounds have water of crystallisation and this is sufficient to cause the reaction to proceed when the solid reagents are mixed. Thus if it is desired to use the solid forms of both the sulfite-containing compound and the choline salicylate, the new compounds will form nevertheless. This is of special importance to the preparation of solid pharmaceutical dosage forms containing choline salicylate In one preferred form of carrying out the invention a solution of choline carbonate is mixed with salicylic acid dissovled in water containing the appropriate quantity of sodium metabisulfite. Care is exercised during the addition of the reagents that the pH of the medium does not exceed the limits of pH 5 to pH 7. The reaction proceeds smoothly and gaseous carbon dioxide is liberated to result in a substantially pure solution of choline salicylate sodium metabisulfite. This solution may be used in further manufacture of pharmaceutical dosage forms or used directly. In place of the sodium metabisulfite described above, one may use another alkali metal metabisulfite, an alkali metal dithionate, an alkali metal bisulfite, an alkali metal hydrosulfite, an alkali metal sulfite and an alkali metal hyposulfite. Gaseous sulfur dioxide may also be used to introduce the sulfite group. The choline salicylate sodium metabisulfite may, if desired, be recovered in solid form although this is not necessary for further pharmaceutical manufacture and the solution of the formed choline salicylate sodium metabisulfite may be used as such.

In practice, it will be found that the new compounds, choline salicylate alkali metal bisulfite, choline salicylate alkali metal metabisulfite, choline salicylate alkali metal sulfite, choline salicylate alkai metal dithionate, chlorine salicylate alkali metal hydrosulfite, choline salicylate alkali metal hyposulfite and choline salicylate sulfite whether in solid form or in solution, will be substantially free of color even after prolonged periods of storge. This may be readily demonstrated by comparing the color formed after heating for 24 hours at 90° C. to 95° C. in an aqueous solution of choline salicylate with that present in a similar treated solution containing an equivalent concentration of the new compounds. When the aforesaid respective solutions are heated for 24 hours at a temperature of from 90° C. to 95° C., a pink color is found to develop in the aqueous solution of choline salicylate whereas the solutions prepared with the new compounds are virtually colorless.

According to another aspect of the invention there is provided a process for the production of solutions of choline salicylate normally having a tendency to form a color qhich comprises the reaction of choline salicylate forming reagents, preferably choline carbonate or choline bicarbonate and salicylic acid, mixed in the presence of an effective amount of an alkali metal sulfite-containing compound, as for example, an alkali metal bisulfite, alkali metal metabisulfite, alkali metal hydrosulfite, alkali metal hyposulfite, alkali metal dithionate, alkali metal sulfite and/or sulfur dioxide whereby the choline salicylate is formed in the presence of the effective amount of said sulfite-containing compound. The aforesaid reaction may be carried out in the presence of water, ethanol, glycerin, propylene glycol, polyoxyethylene glycol or mixtures of the same. Gentle warming may be utilized to remove any of the volatile by-products and the resulting solution of choline salicylate is sufficiently pure for use as such or as an ingredient in further pharmaceutical manufacture. In this manner, appropriate solutions of choline salicylate ranging in concentrations up to 90 percent by weight of choline salicylate, may be obtained in substantially pure form that do not show evidence of color formation even upon prolonged storage. The effective concentration of the alkali metal sulfite-containing compound described above is at least 0.01 percent by weight and not more than 5.0 percent by weight, with a preferred range being from 0.05 percent to 2.5 percent by weight based upon the weight of choline salicylate active ingredient.

It may be found desirable to introduce the sulfite-containing compound in the form of gaseous sulfur dioxide in which event, the effective quantity of sulfur dioxide to be used is the same as described above for the effective amounts of the alkali metal sulfite-containing compounds. An advantage of gaseous sulfur dioxide is the avoidance of the introduction of alkali metal ions which may not be desirable in pharmaceutical preparations intended to treat certain pathologic states.

Still another method for the producion of solutions of choline salicylate substantially free of color is to add an effective quantity of the respective new choline salicylate sulfite-containing compound, as for example, choline salicylate sulfite, choline salicylate alkali metal bisulfite, choline salicylate alkali metal metabisulfite, choline salicylate alkali metal dithionate, choline salicylate akali metal hydrosulfite, choline salicylate alkali metal hyposulfite and choline salicylate alkali metal sulfite to a solution of choline salicylate. When it is desired to utilize the aforesaid choline salicylate sulfite-containing compounds to stabilize a preparation containing choline salicylate, whether in the liquid or solid form, then a quantity of the aforesaid choline salicylate sulfite-containing compound of not less than 0.01 percent by weight is used and not more than 5.0 percent by weight, with a preferred range from 0.05 percent to 2.5 percent by weight, based upon the volume or weight of the active ingredient being stabilized. In achieving this stabilizing effect, then an appropriate quantity of the aforesaid stabilizing compound is added to a solution of choline salicylate in the appropriate quantity after the synthesis of choline salicylate or it may be incorporated in appropriate quantities to the finished pharmaceutical formulation containing choline salicylate. In either event, the resultant product wil be substantially free from color formation. In this manner, pharmaceutical preparations such as solutions, gels, ointments, tablets, lozenges, capsules and suppositories containing choline salicylate may be prepared to be substantially color-free for prolonged periods of time.

The choline salicylate sulfite-containing compounds have the further advantage of suppressing color formation in pharmaceutical preparations containing salicylate compounds such as aspirin salicylic acid, metallic salts of salicylic acid, para-aminosalicylic acid, metallic salts of para-amino salicylic acid, esters of salicylic acid such as methyl salicylate and menthyl salicylate and N-methylglucamine salicylate. Such pharmaceutical preparations may be rendered free of color formation by the addition of the aforesaid choline salicylate sulfite-containing compounds to said salicylate-containing pharmaceutical preparations and the amount of choline salicylate sulfite-containing compound to be added to suppress color formation is not less than 0.1 percent by weight and not more than 5.0 percent by weight of the choline salicylate sulfite-containing compound, based upon the amount of salicylate active ingredient in the preparation to be stabilized.

In practice, the stabilizing choline salicylate sulfite-containing compound is mixed either with the salicylate active ingredient or it may be incorporated into the formulation prior to the finishing step. The sequence for the addition of the preservative compound will depend upon the nature of the pharmaceutical preparation being stabilized. When immiscible substances are utilized, as for example, oil, water systems, it is the water phase which should receive the preservative compound, even though the active salicylate compound may be dissolved in the oil phase.

Thus, should it be desired to stabilize a table containing a salicylate compound, as for example, N-methylglucamine salicylate, aspirin, or metallic salt of salicylic acid, then not less than 0.1 percent by weight and not more than 0.5 percent by weight of the selected choline salicylate sulfite-containing compound is mixed with the salicylate active ingredient. The mixture is then added to appropriate diluents, binding and granulating agents and the whole granulated to prepare a granulation tableting mix. The mixture is then compressed into unit tablets of suitable size and shape containing the desired quantity of active ingredient. The finished tablets will remain substantially free of color for prolonged periods of time.

An alternate procedure for stabilizing the aforesaid salicylate-containing tablet is to add the selected choline salicylate sulfite-containing compound to the mixture of the selected salicylate compound, diluent, binders and granulating agents prior to the granulation step. In this event, the stabilizing compound is thoroughly mixed with the granulation mixture to assure a uniform dispersion.

In a similar manner, the choline salicylate sulfite-containing compound may be mixed with the appropriate salicylate active ingredient prior to its incorporation in an ointment, gel or solution. When it is intended to preserve a salicylate solution against a color formation, then the preservative compound is preferably added prior to the introduction of, or concommitantly with, the salicylate active ingredient, although a beneficial preservative effect will be observed if the stabilizing compound is added prior to the finishing step.

The following examples illustrate the present invention but it is not intended to be limited thereby.

EXAMPLE 1

To an 0.5 molar aqueous solution of choline carbonate is added 52.5 grams of sodium bisulfite (anhydrous) and 69.0 grams of salicylic acid. Each of the solid reagents are added alternately in small increments and with constant stirring. The pH of the solution is determined immediately after the addition of each increment to avoid a drop in the pH of the solution below pH 4. When all of the solid reagents have been added and the ebullition of carbon dioxide has stopped, the solution is gently warmed to 35° C. to remove any residual dissolved carbon dioxide. The solution of choline salicylate sodium bisulfite, thus formed, is essentially color-free and is in a sufficient state of purity to be used as such or for further pharmaceutical manufacture. The compound, choline salicylate sodium bisulfite analyzes in good agreement with its theroetical values for salicylate content. Calculated: 57 percent, by weight, salicylate moiety based upon the weight of choline salicylate: Found: 56.9 percent of salicylate moiety.

On heating the solution of the formed choline salicylate sodium bisulfite for 24 hours at a temperature of from 90° C. to 95° C., there is virtually no change from the original color. The pH of the solution of choline salicylate sodium bisulfite is between pH 6 and pH 6.8.

The electrical conductivity of an 0.5 molar solution of choline salicylate sodium bisulfite determined at 25° C. is $6.654 \times 10^{-3}$. The specific electrical conductivity of an 0.5 molar aqueous solution of choline salicylate is $3.448 \times 10^{-2}$. The specific electrical conductivity of 0.5 molar solution of sodium bisulfite is $9.9125 \times 10^{-2}$. The calculated specific electrical conductivity for a mixture comprising an 0.5 molar solution of choline salicylate and an 0.5 molar sodium bisulfite solution is $13,3605 \times 10^{-2}$, based upon their arithmetic sum of the values. The difference in electrical conductivity exhibited by choline salicylate sodium bisulfite and that of its component moieties establish the formation of a new compound.

EXAMPLE 2

To 500 cc. of propylene glycol is added 82.6 grams of choline bicarbonate, and the mixture is stirred until complete solution is achieved. 95.06 grams of sodium metabisulfite and 69.0 grams of salicyclic acid are added in small increments while controlling the pH to be between pH 4.5 and pH 7. The mixture is stirred until the ebullition of carbon dioxide has stopped. Gentle warming may be used to achieve solution and to facilitate the removal of carbon dioxide. The solution contains the formed choline salicylate sodium metabisulfite.

A representative sample of the formed choline salicylate sodium metabisulfite solution is diluted with sufficient distilled water to provide a concentration of 0.1 molar choline salicylate sodium metabisulfite and the specific electrical conductivity was determined to be $1.064 \times 10^{-2}$. The specific electrical conductivity for 0.1 molar solution of choline salicylate is $4.19 \times 10^{-3}$ and the specific electrical conductivity for 0.1 molar solution of sodium metabisulfite is $1.46 \times 10^{-2}$. The decrease in specific electrical conductivity for the compound, choline salicylate sodium metabisulfite when compared with the arithmetic sum of the conductivities for the mixture of the separate moieties establishes the formation of a new compound.

EXAMPLE 3

To a suitable vessel containing 100 cc. of distilled water is added 14 grams of choline chloride and 17.4 grams of sodium hydrosulfite. The mixture is stirred to achieve solution and 16 grams of sodium salicylate, dissolved in 100 cc. of water are added. The solvent is removed under vacuum to obtain a slurry which is dissolved in absolute methanol and filtered. Anhydrous ether is added to the point of cloudiness and the whole set aside in an ice chest to crystallize. The crystalline material is collected, dried under vacuum to result in the hygroscopic crystalline salt, choline salicylate sodium hydrosulfite. The specific electrical conductivity determined for an 0.1 molar solution of choline salicylate sodium hydrosulfite is $8.8 \times 10^{-4}$. This value is less than the sum of the individual specific electrical conductivities for the separate moieties.

EXAMPLE 4

In a suitable vessel containing 100 ml. of distilled water is added 0.1 mol of choline citrate and 0.1 mol of lithium salicylate. The mixture is stirred until complete solution is achieved. The solvent is removed by vacuum distillation and the residue dissolved in anhydrous amyl alcohol and filtered. The solution is set aside to crystallize in an ice chest after the addition of sufficient acetone to cause clouding. The crystallized lithium citrate is removed by filtration and the filtrate concentrated under vacuum. To the residue is added 250 cc. of 0.1 molar aqueous solution of sodium hyposulfite and the mixture is filtered and the solvent removed once again under vacuum to yield choline salicylate sodium hyposulfite.

The specific electrical conductivity determined for an 0.5 molar solution of choline salicylate sodium hyposulfite is $6.31 \times 10^{-3}$, which is less than the caluclated sum of the specific electrical conductivities determined for an equimolar concentration of the separate moieties.

EXAMPLE 5

To an aqueous solution consisting of 5 grams of choline salicylate, dissolved in 100 ml. of distilled water is added 72.6 grams of sodium dithionate. The mixture is stirred and filtered. The filtrate contains the solution of choline salicylate sodium dithionate which may be used in further pharmaceutical manufacture or dispensed as such. The arithmetic sum of the specific electrical conductivity for equimolar concentrations of sodium dithionate and choline salicylate is $9.82 \times 10^{-2}$. The specific electrical conductivity of an 0.25 molar solution of choline salicylate sodium dithionate is $5.36 \times 10^{-3}$, which is less than the calculated sum of the separate values.

EXAMPLE 6

To an aqueous solution containing 28.5 grams of choline carbonate is added 13.8 grams of salicylic acid and 12.6 grams of sodium sulfite. The mixture is stirred until complete solution is achieved and the ebullition of gases cease. The solution of choline salicylate sodium sulfite thus formed is sufficiently pure to be used for further pharmaceutical manufacture. The compound choline salicylate sodium sulfite may be obtained by removing the solvent under high vacuum with the aid of gentle warming. The compound is a colorless crystal, that is highly hygroscopic, rapidly absorbing water on exposure to the atmosphere. An 0.1 molar solution of choline salicylate sodium sulfite has a specific electrical conductivity of $8.16 \times 10^{-3}$.

EXAMPLE 7

In a three-neck round-bottom flask fitted with a stirring rod, a gas inlet tube and an exhaust vent fitted with a trap, is placed 100 ml. of 0.1 molar aqueous solution of choline salicylate. The stirring is started and the solution cooled to about 0° C. Gaseous sulfur dioxide is then passed through the solution until the rise in the net weight of the solution is 8 grams. Care is taken that the temperature of the solution does not rise above 5° C. When the required quantity of sulfur dioxide has been added, the stirring is continued while the solution warms to room temperature. An equal volume of distilled water is added and the resulting solution containing the formed choline salicylate sulfur dioxide is in sufficiently pure form for use as such or for further pharmaceutical manufacture. The 0.05 molar solution of choline salicylate sulfite has a specific electrical conductivity of $9.87 \times 10^{-4}$.

EXAMPLE 8

In place of sodium bisulfite used as described in Example 1 above; sodium metabisulfite, used as described in Example 2 above; sodium hydrosulfite used as described in Example 3 above; sodium hyposulfite used as described in Example 4 above; sodium dithionate used as described in Example 5 above, and sodium sulfite used as described in Example 6 above, there may be substituted in equimolar proportions a compound selected from the group consisting of sodium sulfite, sodium bisulfite, sodium metabisulfite, sodium dithionate, sodium hydrosulfite, sodium hyposulfite, lithium sulfite, lithium bisulfite, lithium metabisulfite, lithium dithionate, lithium hydrosulfite, lithium hyposulfite, potassium sulfite, potassium bisulfite, potassium metabisulfite, potassium dithionate, potassium hydrosulfite and potassium hyposulfite. The remainder of the steps being the same the respective choline salicylate alkali metal sulfite-containing compound is formed. An 0.05 molar aqueous solution of the aforesaid formed choline salicylate alkali metal sulfite-containing compound has the following specific electrical conductivity.

| Compound | Electrical Resistance (ohms) | Specific Electrical Conductivity ($\times 10^{-9}$ mhos) |
|---|---|---|
| Choline Salicylate Sodium Sulfite | 41.1 | 1.93 |

-continued

| Compound | Electrical Resistance (ohms) | Specific Electrical Conductivity ($\times 10^{-9}$ mhos) |
|---|---|---|
| Choline Salicylate Sodium Bisulfite | 30.4 | 2.61 |
| Choline Salicylate Sodium Metabisulfite | 18.8 | 4.21 |
| Choline Salicylate Sodium Dithionate | 16.8 | 4.71 |
| Choline Salicylate Sodium Hydrosulfite | 34.3 | 2.31 |
| Choline Salicylate Sodium Hyposulfite | 27.3 | 2.93 |
| Choline Salicylate Potassium Sulfite | 37.2 | 2.13 |
| Choline Salicylate Potassium Bisulfite | 26.3 | 3.01 |
| Choline Salicylate Potassium Metabisulfite | 15.5 | 5.13 |
| Choline Salicylate Potassium Dithionate | 17.3 | 4.50 |
| Choline Salicylate Potassium Hydrosulfite | 22.0 | 3.61 |
| Choline Salicylate Potassium Hyposulfite | 25.4 | 2.12 |
| Choline Salicylate Lithium Sulfite | 37.2 | 2.13 |
| Choline Salicylate Lithium Bisulfite | 28.2 | 2.81 |
| Choline Salicylate Lithium Metabisulfite | 16.2 | 4.89 |
| Choline Salicylate Lithium Dithionate | 15.6 | 5.07 |
| Choline Salicylate Lithium Hydrosulfite | 27.3 | 2.91 |
| Choline Salicylate Lithium Hyposulfite | 23.2 | 3.42 |

The specific electrical conductivity for an 0.05 molar solution of the separate reagents is:

| Reagent | Electrical Resistance (ohms) | Specific Electrical Conductance ($\times -10^{-9}$ mhos) |
|---|---|---|
| Sodium sulfite | 51.4 | 1.543 |
| Sodium bisulfite | 34.3 | 2.31 |
| Sodium metabisulfite | 18.17 | 4.36 |
| Sodium dithionate | 17.1 | 4.637 |
| Sodium hydrosulfite | 39.9 | 1.937 |
| Sodium hyposulfite | 29.9 | 2.652 |
| Lithium sulfite | 49.6 | 1.764 |
| Lithium bisulfite | 37.1 | 2.137 |
| Lithium metabisulfite | 17.9 | 4.430 |
| Lithium dithionate | 17.0 | 4.663 |
| Lithium hydrosulfite | 37.7 | 2.103 |
| Lithium hyposulfite | 28.9 | 2.744 |
| Potassium sulfite | 47.2 | 1.680 |
| Potassium bisulfite | 32.1 | 2.470 |
| Potassium metabisulfite | 16.9 | 4.692 |
| Potassium dithionate | 16.3 | 4.330 |
| Potassium hydrosulfite | 26.1 | 3.030 |
| Potassium hyposulfite | 26.7 | 2.970 |
| Choline salicylate | 78.4 | 1.01 |

EXAMPLE 9

To 100 ml. of a 50 percent solution of choline carbonate, dissolved in distilled water, is added 0.25 grams of sodium bisuflite. The mixture is stirred until solution is achieved. To this solution is then added 27.6 grams of salicylic acid in small increments while stirring. Carbon dioxide is liberated and when the ebulliton of gas ceases, the aqueous solution of choline salicylate thus formed contains a stabilizing quantity of choline salicylate sodium bisulfite and said solution may be dispensed directly in unit dosage form to achieve its intended therapeutic effect.

Should a liquid pharmaceutical preparation be desired, other than a solution, as for example, a syrup, then the appropriate quantity of sugar is added after the ebullition of carbon dioxide ceases. When an elixir is intended, then the proper quantity of ethanol is added for part of the water used to form the solution of choline carbonate. Glycerin, propylene glycol and polyoxyethylene glycol may be used to form a liquid solution for dispensing and the aforesaid solvents may be used to replace the water and/or the ethanol described above. Glycerin, propylene glycol and polyoxyethylene glycol may be the sole solvent or used as mixtures of the same or mixed with water, alcohol or their mixtures. Flavoring materials may be added when desired.

In place of the sodium bisulfite described above, there may be substituted in equimolar proportions a compound selected from the group consisting of sodium sulfite, sodium metabisulfite, sodium dithionate, sodium hydrosulfite, sodium hyposulfite, lithium sulfite, lithium bisulfite, lithium metabisulfite, lithium dithionate, lithium hydrosulfite, lithium hyposulfite, potassium sulfite, potassium bisulfite, potassium metabisulfite, potassium dithionate, potassium hydrosulfite and potassium hyposulfite.

EXAMPLE 10

To a freshly prepared solution containing 50 grams of choline salicylate per 100 ml. is added 1.25 grams of choline salicylate sodium metabisulfite. The mixture is stirred, filtered and packaged in unit dosage form for dispensing. The new pharmaceutical composition will be substantially free of color even on prolonged storage. The solvent to prepare said solution may be water, ethanol, glycerin, propylene glycol, polyoxyethylene glycol or mixtures of the same. Appropriate flavors may be added if desired.

In place of the choline salicylate sodium metabisulfite described above, there may be substituted in equal weight a compound selected from the group consisting of choline salicylate sodium sulfite, choline salicylate sodium bisulfite, choline salicylate sodium dithionate, choline salicylate sodium hydrosulfite, choline salicylate hyposulfite, choline salicylate potassium sulfite, choline salicylate potassium bisulfite, choline salicylate potassium metabisulfite, choline salicylate potassium dithionate, choline salicylate potassium hydrosulfite, choline salicylate potassium hyposulfite, choline salicylate lithium sulfite, choline salicylate lithium bisulfite, choline salicylate lithium metabisulfite, choline salicylate lithium dithionate, choline salicylate lithium hydrosulfite, choline salicylate lithium hyposulfite, in similar concentration to that described for choline salicylate sodium metabisulfite. The optimal effective range for color stabilization for the said choline salicylate alkali metal sulfite-containing compounds described above is not less than 0.01 percent by weight and not more than 5.0 percent by weight and preferably 0.5 percent to 2.5 percent by weight based on the weight of active salicylate compound used.

EXAMPLE 11

When a solid dosage form is desired, as for example, capsules, tablets, ointments or gels, then either a concentrated solution of choline salicylate, as for example, containing from 80 percent to 90 percent by weight of choline salicylate, or the solid form of choline salicylate is used. The stabilizing new compound, as for example, choline salicylate lithium metabisulfite, 0.05 percent by weight, is added to the choline salicylate prior to its incorporation into the base or vehicle. The remainder of the steps required to prepare the respective pharmaceutical preparation is well known to the art and remains the same and the resulting product will be found to be free of color formation even on prolonged storage.

When preparing a tablet, such carriers and/or diluents as magnesium sulfate, lactose, sucrose, starch or mixtures of the same may be used with either a concentrated solution of choline salicylate or its dry form. After the incorporation of the active ingredients and the stabilizing compound with the diluent and/or carrier, suitable granulating agents and tablet lubricants may be added. Tablets of suitable size containing the appropriate quantity of choline salicylate are then prepared by compression.

When capsules are preferred, a mixture of the above described carrier plus the active ingredient and the appropriate quantity of the color-stabilizing new compound described herein, are filled directly into capsules of appropriate size and shape.

When ointments, gels and suppositories are desired, then the active ingredients and selected color-stabilizing new compound are mixed and added to the appropriate pharmaceutically acceptable ointment base, gel vehicle or suppository base and the whole milled to achieve a uniform distribution. The finished ointment or gel preparation is then packaged in unit dosage form for dispensing while the suppository mass is shaped into suppositories of suitable size for dispensing.

EXAMPLE 12

In place of the choline salicylate used to form the choline salicylate sulfite-containing compound, there may be substituted in equimolar quantities, N-methylglucamine salicylate, aspirin, para-amino salicylate and its metal salts, salicylic acid and its metal salts, and esters of salicylic acid, to form corresponding salicylate sulfite-containing compounds. Said corresponding salicylate alkali metal sulfite-containing compound, prepared in the manner set forth above, possesses the same property of suppressing color formation in pharmaceutical compositions as does choline salicylate sulfite-containing compounds. The formed corresponding salicylate sulfite-containing compounds have the full pharmaco-therapeutic properties of the respective salicylate moieties, such as analgesia, antipyretic and local anti-inflammatory actions, while the para-amino salicylate alkali metal sulfite-containing compounds have in addition, an anti-tubercular action. The above new compounds may be used in therapy as liquid or solid pharmaceutical preparations administered either orally, topically or rectally.

EXAMPLE 13

When it is desired to suppress the color in a salicylate-containing pharmaceutical preparation then not less than 0.1 percent by weight and not more than 5.0 percent by weight of the appropriate choline salicylate sulfite-containing compound is incorporated into the salicylate-containing pharmaceutical preparation intended to be stabilized against color formation. Pharmaceutical preparations containing such salicylate compounds as aspirin, salicylic acid, metallic salts of salicylic acid, para-aminosalicylic acid, metallic salts of para-aminosalicylic acid, esters of salicylic acid such as methyl salicylate and menthyl salicylate and N-methylglucamine salicylate may be rendered free of color formation through the use of the aforesaid new compounds. The particular salicylate-containing pharmaceutical dosage form to be stabilized may be either a solid dosage form as for example, tablets, powders, lozenges, suppositories, ointments, creams, gels or a liquid dosage form as for example, solutions, tinctures, elixirs and syrups.

In achieving color stabilization of a salicylate-containing pharmaceutical preparation, as for example, a gel, then 8.72 grams of N-methylglucammonium salicylate are mixed with 0.05 grams of choline salicylate sodium metabisulfite and the whole dissolved in 40 cc. of ethyl alcohol. When solution is complete, cetyldimethylbenzylammonium chloride, 0.01 gram, is added to the ethanol and the whole filtered. Suitable flavoring agents may be added, if desired, to the alcohol solution.

In a separate flask containing 40 ml. of distilled water is dispersed 2.75 grams of methyl cellulose-4000 and 5 grams of glycerin. The solution is heated to approximately 50° C. and mixed with the aforesaid alcohol solution. The mixture is filtered and the pH adjusted so that it is between pH 5 and pH 7. The mixture is rapidly chilled to form a gel, which is then packaged in unit containers. The resultant gel will be free of color formation, even after storage for prolonged periods of time.

When it is desired to stabilize an emulsion containing a salicylate compound, as for example, menthyl salicylate, then 0.25 gram of choline salicylate sodium bisulfite is dissolved in 50 ml. of peanut oil and to this is added 1 gram of menthyl salicylate. Warming may be used to facilitate solution. In a separate vessel containing 50 ml. of distilled water is added 2 grams of sorbitolmono-oleate and the aqueous solution added to the peanut oil and the whole homogenized. The resultant preparation is a white emulsion useful as a sun-screen dermatologic preparation will not form a color even on prolonged storage.

To an 0.5 gram of choline salicylate potassium sulfite is added 100 grams of para-aminosalicylic acid and the mixture tumbled until a uniform dispersion results. The resultant bulk powder may be stored for prolonged periods of time without a change in color and may be used in further pharmaceutical manufacture.

What is claimed is:

1. The method for suppressing color formation in a salicylate-containing pharmaceutical formulation comprising incorporating an effective amount of between 0.1 to 5.0 percent by weight of a choline salicylate sulfite-containing compound selected from the group consisting of choline salicylate sulfite, choline salicylate sodium sulfite, choline salicylate sodium bisulfite, choline salicylate sodium metabisulfite, choline salicylate sodium dithionate, choline salicylate sodium hydrosulfite, choline salicylate sodium hyposulfite, choline salicylate potassium sulfite, choline salicylate potassium bisulfite, choline salicylate potassium metabisulfite, choline salicylate potassium dithionate, choline salicylate potassium hydrosulfite, choline salicylate potassium hyposulfite, choline salicylate lithium sulfite, choline salicylate lithium busulfite, choline salicylate lithium metabisulfite, choline salicylate lithium dithionate, choline salicylate lithium hydrosulfite, choline salicylate lithium hyposulfite to a salicylate-containing pharmaceutical dosage form.

2. The method of claim 1 said choline salicylate sulfite-containing compound being choline salicylate sodium bisulfite and said salicylate-containing pharmaceutical dosage form being choline salicylate syrup.

3. This method of claim 1 said choline salicylate sulfite-containing compound being choline salicylate sodium bisulfite and said salicylate-containing pharmaceutical dosage form being choline salicylate tablets.

4. The method of claim 1 said choline salicylate sulfite-containing compound being choline salicylate sodium bisulfite and said salicylate-containing pharmaceutical dosage form being choline salicylate gel.

5. The method of claim 1 said choline salicylate sulfite-containing compound being choline salicylate sodium bisulfite and said salicylate-containing pharmaceutical dosage form being choline salicylate solution.

6. The method of claim 1 said choline salicylate sulfite-containing compound being choline salicylate sodium bisulfite and said salicylate-containing pharmaceutical dosage form being choline salicylate ear drops.

7. The method of claim 1 said choline salicylate sulfite-containing compound being choline salicylate sodium metabisulfite and said salicylate-containing pharmaceutical dosage form being choline salicylate syrup.

8. The method of claim 1 said choline salicylate sulfite-containing compound being choline salicylate sodium metabisulfite and said salicylate-containing pharmaceutical dosage form being choline salicylate tablets.

9. The method of claim 1 said choline salicylate sulfite-containing compound being choline salicylate sodium metabisulfite and said salicylate-containing pharmaceutical dosage form being choline salicylate gel.

10. The method of claim 1 said choice salicylate sulfite-containing compound being choline salicylate sodium metabisulfite and said salicylate-containing pharmaceutical dosage form being choline salicylate solution.

11. The method of claim 1 said choline salicylate sulfite-containing compound being choline salicylate metabisulfite and said salicylate-containing pharmaceutical dosage form being choline salicylate ear drops.

12. The method of claim 1 said choline salicylate sulfite-containing compound being choline salicylate potassium sulfite and said salicylate-containing pharmaceutical dosage form being aspirin tablets.

13. The method of claim 1 said choline salicylate sulfite-containing compound being choline salicylate sodium metabisulfite and said salicylate-containing pharmaceutical dosage form being N-methylglucamine salicylate bulk powder.

14. The method of claim 1 said choline salicylate sulfite-containing compound being choline salicylate sodium sulfite and said salicylate-containing pharmaceutical dosage form being menthyl salicylate emulsion.

15. The method of claim 1 said choline salicylate sulfite-containing compound being choline salicylate sodium metabisulfite and said salicylate-containing pharmaceutical dosage form being methyl salicylate ointment.

16. The method of claim 1 said choline salicylate sulfite-containing compound being choline salicylate potassium sulfite and said salicylate-containing pharmaceutical dosage form being para-aminosalicylic acid bulk powder.

* * * * *